United States Patent
Yuan et al.

(10) Patent No.: US 8,564,788 B2
(45) Date of Patent: Oct. 22, 2013

(54) OPTICAL IMAGING METHOD AND OPTICAL IMAGING APPARATUS

(75) Inventors: Zhijia Yuan, River Edge, NJ (US);
Zhenguo Wang, Fort Lee, NJ (US);
Kinpui Chan, Ridgewood, NJ (US)

(73) Assignee: Kabushiki Kaisha Topcon, Tokyo (JP)

( * ) Notice: Subject to any disclaimer, the term of this patent is extended or adjusted under 35 U.S.C. 154(b) by 212 days.

(21) Appl. No.: 13/190,676

(22) Filed: Jul. 26, 2011

(65) Prior Publication Data

US 2013/0027712 A1    Jan. 31, 2013

(51) Int. Cl.
*G01B 9/02* (2006.01)

(52) U.S. Cl.
USPC ......................................................... 356/479

(58) Field of Classification Search
USPC ........ 356/456, 479, 497; 250/227.19, 227.27; 600/476
See application file for complete search history.

(56) References Cited

U.S. PATENT DOCUMENTS

| | | | | |
|---|---|---|---|---|
| 5,321,501 | A * | 6/1994 | Swanson et al. | 356/479 |
| 7,079,254 | B2 * | 7/2006 | Kane et al. | 356/456 |
| 7,330,270 | B2 * | 2/2008 | O'Hara et al. | 356/479 |
| 7,433,046 | B2 * | 10/2008 | Everett et al. | 356/479 |

FOREIGN PATENT DOCUMENTS

WO    2006-127952 A2    11/2006

OTHER PUBLICATIONS

Wojtkowski, M., et al. Full range complex spectral optical coherence tomography technique in eye imaging. In: Optics Letter; vol. 27, No. 16; Aug. 15, 2002; pp. 1415-1417.
Leitgeb, R.A., et al. Phase-shifting algorithm to achieve high-speed long-depth-range probing by frequency-domain optical coherence tomography. In: Optics Letter; vol. 28, No. 22; Nov. 15, 2003; pp. 2201-2203.
Gotzinger, E., et al. High speed full range complex spectral domain optical coherence tomography. In: Opt Express, 13(2); Jan. 24, 2005; pp. 583-594.
Wang, R.K. Fourier domain optical coherence tomography achieves full range complex imaging in vivo by introducing a carrier frequency during scanning. In: Physics in Medicine and Biology; 52(19); Sep. 14, 2007; pp. 5897-5907.
Leitgeb, R.A., et al. Complex ambiguity-free fourier domain optical coherence tomography through transverse scanning. In: Optics Letters; vol. 32, No. 23; Dec. 1, 2007; pp. 3453-3455.
An, L, et al. Use of a scanner to modulate spatial interferograms for in vivo full-range fourier-domain optical coherence tomography. In: Optics Letters; vol. 32, No. 23; Dec. 1, 2007; pp. 3423-3425.

(Continued)

*Primary Examiner* — Michael A Lyons
(74) *Attorney, Agent, or Firm* — Pearne & Gordon LLP

(57) ABSTRACT

An optical imaging method is provided that can realize, at low cost, the extension of the imaging depth range. An optical imaging apparatus 400 is an apparatus that forms a tomographic image of an object using FD-OCT, and performs a scanning step, detection step and imaging step. In the scanning step, the object is scanned with a signal light while alternately changing the phase difference between the signal light and a reference light to two preset phase differences. In the detection step, interference light of the signal light passing through the object and the reference light is detected. In the imaging step, a tomographic image of the object is formed based on the detection results of a plurality of the interference lights sequentially obtained in the detection step according to the scanning.

18 Claims, 12 Drawing Sheets

(56) References Cited

OTHER PUBLICATIONS

Yasuno, Y., et al. Simultaneous B-M-mode scanning method for real-time full-range fourier domain optical coherence tomography. In: Applied Optics; vol. 45, No. 8; Mar. 10, 2006; pp. 1861-1865.

Vergnole, S., et al. Artifact removal in fourier-domain optical coherence tomography with a piezoelectric fiber stretcher. In: Optics Letters; vol. 33, No. 7; Apr. 1, 2008; pp. 732-734.

Makita, S., et al. Full-range, high-speed, high-resolution 1-μm spectral-domain optical coherence tomography using BM-scan for volumetric imaging of the human posterior eye. In: Optics Express; vol. 16, No. 12; Jun. 9, 2008; pp. 8406-8420.

Yun, S.H., et al. Removing the depth-degeneracy in optical frequency domain imaging with frequency shifting. In: Optics Express; vol. 12, No. 20; Ocotber 4, 2004; pp. 4822-4828.

Zhang, J., et al. Removal of a mirror image and enhancement of the signal-to-noise ratio in fourier-domain optical coherence tomography by use of an electro-optical phase modulator. In: Optics Letters; vol. 30, No. 2; Jan. 15, 2005; pp. 147-149.

Choma, M.A., et al. Instantaneous quadrature low-coherence interferometry with 3×3 fiber-optic couplers. In: Optics Letters; vol. 28, No. 22; Nov. 15, 2003; pp. 2162-2164.

Sarunic, M.V., et al. Real-time quadrature projection complex conjugate resolved fourier domain optical coherence tomography. In: Optics Letters; vol. 31, No. 16; Aug. 15, 2006; pp. 2426-2428.

Mao, Y., et al. 3×3 Mach-Zehnder interferometer with unbalanced differential detection for full-range swept-source optical coherence tomography. In: Applied Optics; vol. 47, No. 12; Apr. 20, 2008; pp. 2004-2010.

Vakhtin, A.B., et al. Resolving the complex conjugate ambiguity in fourier-domain OCT by harmonic lock-in detection of the spectral interferogram. In? Optics Letters; vol. 31, No. 9; May 1, 2006; pp. 1271-1273.

Wang, K., et al. Sinusoidal B-M method based spectral domain optical coherence tomography for the elimination of complex-conjugate artifact. In: Optics Express; vol. 17, No. 19; Sep. 14, 2009; pp. 16820-16833.

Tao, Y.K., et al. High-speed complex conjugate resolved retinal spectral domain optical coherence tomography using sinusoidal phase modulation. In: Optics Letters; vol. 32, No. 20; Oct. 15, 2007; pp. 2918-2920.

Vakhtin, A.B., et al. Demonstration of complex-conjugate-resolved harmonic fourier-domain optical coherence tomography imaging of biological samples. In: Applied Optics; vol. 46, No. 18; Jun. 20, 2007; pp. 3870-3877.

\* cited by examiner

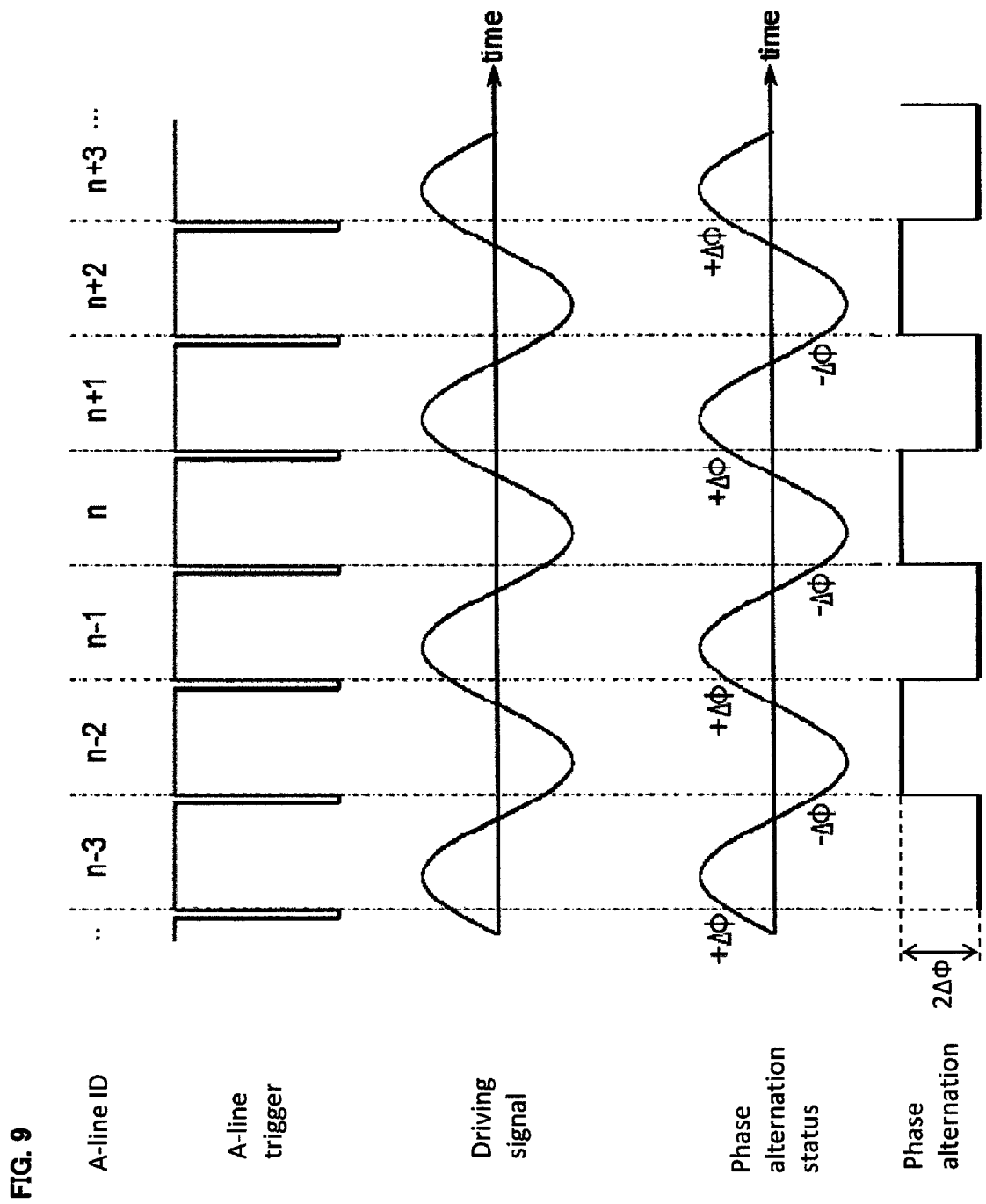

OPTICAL IMAGING METHOD AND OPTICAL IMAGING APPARATUS

FIELD OF THE INVENTION

The present invention relates to an optical imaging method and an optical imaging apparatus using optical coherence tomography.

BACKGROUND OF THE INVENTION

Optical coherence tomography (abbreviated OCT) is a technique for forming a tomographic image of an object by detecting the interference light of a signal light passing through the object and a reference light. The OCT is used in, for example, the medical field due to the advantage of high resolution images being obtained quickly and non-invasively.

The major advance in this technique is Fourier domain OCT (abbreviated FD-OCT). With FD-OCT, a measurement speed several dozen to several hundred times faster compared to conventional time domain OCT (abbreviated TD-OCT) can be achieved.

FD-OCT includes spectral domain OCT (abbreviated SD-OCT) in which the interference light is detected through spectral decomposition and swept source OCT (abbreviated SS-OCT) in which interference lights of various wavelengths are obtained using a wavelength-swept light source.

The detected spectrum in SD-OCT and SS-OCT, i.e., a spectral interferogram (interference spectrum), is expressed by the following equation:

$$I(k) = s(k) \cdot \left( I_R + I_S + \int_{-\infty}^{+\infty} 2\sqrt{I_R I_S} \cos(kz + \varphi_0(z)) dz \right) \quad (1)$$

Here, k, s(k), z, $I_R$, $I_S$ and $\varphi_0(z)$ represent the wave number, the light source spectrum, the path length difference between the signal arm and the reference arm, the back reflection of the reference light from the reference mirror (reference light), the auto correlation term of the signal light passing through the object, and an initial phase term, respectively. In general, $I_R$ and $I_S$ are low frequency signals or background components (DC components) that can be easily removed. Consequently, Equation (1) is simplified as the following.

$$I(k) = \int_{-\infty}^{+\infty} A(z) \cos(kz + \varphi_0(z)) dz \quad (2)$$

Here, $A(z) = s(k) \cdot 2\sqrt{(I_R I_S)}$ represents the back scattering coefficient of the object at depth z. Based on Equation (2), using a Fourier-transform of I(k), the back-scattering profile of the object at the depth z, i.e., the A-line profile, can be reconstructed.

However, because the spectral interferogram is detected in real values, the reconstructed A-line profile suffers from complex conjugate ambiguity. The complex conjugate ambiguity means that a signal at z=Δz and a signal at z=−Δz cannot be differentiated from each other. As a result, the possible imaging depth of FD-OCT is shrunk by half.

This shrinkage of the possible imaging depth due to the complex conjugate ambiguity will be explained with reference to FIG. 11A-FIG. 11C. FIG. 11A shows a true image T of the object drawn in the full frame F0. However, when reconstructing the image from the interferogram consisting of a real value, the mirror image T' (complex conjugate artifact) as well as the true image T appears as shown in FIG. 11B. In order to avoid such a complex conjugate ambiguity, the measurement depth of the object is shifted to separate the true image T and the mirror image T' from each other (see FIG. 11C). As a result, only the lower half F of the frame F0 of the reconstructed image is the drawing range of the true image T. That is, the upper half of the frame F0 is wasted, and the imaging depth is halved. Consequently, the demand to obtain the broadest possible image range is restricted.

Various techniques have been developed to remove or suppress this problem of such a complex conjugate ambiguity. These techniques include phase shifting (non-patent documents 1-3), BM mode scanning (non-patent documents 4-9), frequency shifting (non-patent documents 10, 11), 3×3 fiber-optical coupler (non-patent documents 12-14), phase modulation (patent document 1, non-patent documents 15-18), etc. However, the implementation of these techniques is limited by certain practical issues as described below.

Phase shifting is a method well known in the field of Fourier optics, in which each spectral interferogram is obtained with different initial phases while moving the reference mirror stepwise by a distance on the order of light wavelengths. Phase shifting-based techniques require accurate phase changes between adjacent A-lines. These techniques are limited by devices such as a piezo stage or electrical phase modulator. Moreover, these techniques are compromised by factors such as mechanical instability of a system and chromatic errors.

BM mode scanning is a technique that is an extension of phase shifting, in which phases are changed during transverse scanning. The method of changing a phase includes a method in which the phase is changed stepwise (non-patent documents 8, 9) and a method in which the phase is changed linearly (non-patent documents 4-7). The former has some of the drawbacks of phase shifting and is not cost-effective in achieving a stepwise phase change. The latter causes an undesirable situation in which the path length is changed when the range of transverse scanning is widened.

Frequency shifting is a method based on frequency separation and is only applicable to SS-OCT. Moreover, frequency shifting requires expensive devices such as EOM (electro-optic modulators) and AOM (acousto-optic modulators) in order to shift the signal to a higher frequency band. As a result, this system also requires significantly high speed data acquisition devices.

3×3 fiber-optical coupler-based techniques suffer from wavelength-dependent coupling coefficients for broadband and require additional costly detectors.

Phase modulation techniques are more recently reported methods, in which complex conjugate artifacts are removed by adding a sinusoidal phase modulation. Phase modulation is usually introduced by a dithering mirror driven by a piezo stage provided with the reference arm. One approach relies on the integration effect of the camera, so its application is restricted to SD-OCT (non-patent document 17). Other approaches extract complex signals from multiple harmonic signals generated by the modulation based on complicated Bessel functions. This causes several major problems. For example, it requires extra decoding hardware, or higher load computation if decoding is performed by software. Moreover, at least 3 harmonic signals of different orders (from 0 order to 2nd order) are involved (non-patent documents 15, 19), and in many cases, 3rd order calibration is even necessary (non-patent documents 16, 18), but these multiple harmonic signals could easily cause aliasing. In other words, when demodulating the modulation signal in phase modulation, at least 3 signals have to be detected, so there is a problem in terms of hardware or software as well as a problem in that a higher measurement band is required in order to detect higher order modulation signals without aliasing.

PRIOR ART DOCUMENTS

Patent Documents

[Patent Document 1] WO 2006/127952

Non-Patent Documents

[Non-patent Document 1] Wojtkowski, M., A. Kowalczyk, R. Leitgeb, and A. F. Fercher, Full range complex spectral optical coherence tomography technique in eye imaging. Opt Lett, 2002. 27(16): p. 1415-7

[Non-patent Document 2] Leitgeb, R. A., C. K. Hitzenberger, A. F. Fercher, and T. Bajraszewski, Phase-shifting algorithm to achieve high-speed long-depth-range probing by frequency-domain optical coherence tomography. Opt. Lett., 2003. 28(22): p. 2201-2203

[Non-patent Document 3] Gotzinger, E., M. Pircher, R. Leitgeb, and C. Hitzenberger, High speed full range complex spectral domain optical coherence tomography. Opt Express, 2005. 13(2): p. 583-94

[Non-patent Document 4] Wang, R. K., Fourier domain optical coherence tomography achieves full range complex imaging in vivo by introducing a carrier frequency during scanning. Applied Physics Letters, 2007. 52(19): p. 5897-907

[Non-patent Document 5] Leitgeb, R. A., R. Michaely, T. Lasser, and S. C. Sekhar, Complex ambiguity-free Fourier domain optical coherence tomography through transverse scanning. Opt. Lett., 2007. 32(23): p. 3453-3455

[Non-patent Document 6] An, L. and R. K. Wang, Use of a scanner to modulate spatial interferograms for in vivo full-range Fourier-domain optical coherence tomography. Opt. Lett., 2007. 32(23): p. 3423-3425

[Non-patent Document 7] Yasuno, Y., S. Makita, T. Endo, G. Aoki, M. Itoh, and T. Yatagai, Simultaneous B-M-mode scanning method for real-time full-range Fourier domain optical coherence tomography. Appl Opt, 2006. 45(8): p. 1861-5

[Non-patent Document 8] Vergnole, S., G. Lamouche, and M. L. Dufour, Artifact removal in Fourier-domain optical coherence tomography with a piezoelectric fiber stretcher. Opt Lett, 2008. 33(7): p. 732-4

[Non-patent Document 9] Makita, S., T. Fabritius, and Y. Yasuno, Full-range, high-speed, high-resolution 1 microm spectral-domain optical coherence tomography using BM-scan for volumetric imaging of the human posterior eye. Opt Express, 2008. 16(12): p. 8406-20

[Non-patent Document 10] Yun, S., G. Tearney, J. de Boer, and B. Bouma, Removing the depth-degeneracy in optical frequency domain imaging with frequency shifting. Opt Express, 2004. 12(20): p. 4822-8

[Non-patent Document 11] Zhang, J., J. S. Nelson, and Z. Chen, Removal of a mirror image and enhancement of the signal-to-noise ratio in Fourier-domain optical coherence tomography using an electro-optic phase modulator. Opt Lett, 2005. 30(2): p. 147-9

[Non-patent Document 12] Choma, M. A., C. Yang, and J. A. Izatt, Instantaneous quadrature low-coherence interferometry with 3×3 fiber-optic couplers. Opt Lett, 2003. 28(22): p. 2162-4

[Non-patent Document 13] Sarunic, M. V., B. E. Applegate, and J. A. Izatt, Real-time quadrature projection complex conjugate resolved Fourier domain optical coherence tomography. Opt Lett, 2006. 31(16): p. 2426-8

[Non-patent Document 14] Mao, Y., S. Sherif, C. Flueraru, and S. Chang, 3×3 Mach-Zehnder interferometer with unbalanced differential detection for full-range swept-source optical coherence tomography. Appl. Opt., 2008. 47(12): p. 2004-2010

[Non-patent Document 15] Vakhtin, A. B., K. A. Peterson, and D. J. Kane, Resolving the complex conjugate ambiguity in Fourier-domain OCT by harmonic lock-in detection of the spectral interferogram. Opt Lett, 2006. 31(9): p. 1271-3

[Non-patent Document 16] Wang, K., Z. Ding, Y. Zeng, J. Meng, and M. Chen, Sinusoidal B-M method based spectral domain optical coherence tomography for the elimination of complex-conjugate artifact. Opt Express, 2009. 17(19): p. 16820-33

[Non-patent Document 17] Tao, Y. K., M. Zhao, and J. A. Izatt, High-speed complex conjugate resolved retinal spectral domain optical coherence tomography using sinusoidal phase modulation. Opt Lett, 2007. 32(20): p. 2918-20

[Non-patent Document 18] Vakhtin, A. B., K. A. Peterson, and D. J. Kane, Demonstration of complex-conjugate-resolved harmonic Fourier-domain optical coherence tomography imaging of biological samples. Appl Opt, 2007. 46(18): p. 3870-7

SUMMARY OF THE INVENTION

Problem to be Solved by the Invention

The object of the present invention is to provide a technique capable of extending the imaging depth range at a lower cost.

Means of Solving the Invention

An optical imaging method for forming a tomographic image of an object by processing an interference spectrum based on an interference light that is obtained by combining a signal light passing through said object and a reference light, characterized in that the method comprises: a scanning step to scan the object with the signal light while alternately changing the phase difference between the signal light and the reference light to two preset phase differences; a detection step to detect the interference light of said signal light passing through said object and said reference light; and an imaging step to form the tomographic image of said object based on the detection results of a plurality of said interference lights sequentially obtained in said detection step according to said scanning.

In said scanning step, said scanning may be performed by sequentially changing the irradiation position of said signal light on said object, and by synchronizing the irradiation timing of said signal light on said object and the changing timing of said phase difference.

In said scanning step, said signal light may be irradiated on said object at a substantially constant time interval, and the frequency for the alternating change of said phase difference is substantially ½ of said time interval.

In said scanning step, the alternating change of said phase difference may be performed by alternately changing the phase of said reference light between two phases.

In said scanning step, the alternating change of said phase difference may be performed by alternately changing the phase of said signal light between two phases.

In said imaging step, a complex interference spectrum consisting of complex numbers may be generated based on the detection results of said interference light, and said tomographic image may be formed based on this complex interference spectrum.

Said process of generating said complex interference spectrum may comprise: a process of obtaining a first interference spectrum by applying a low pass filter to the interference spectrum based on the detection results of said interference light, and obtaining a real part by dividing said first interference spectrum by the cosine of said phase difference; a process of obtaining a second interference spectrum by multiplying the interference spectrum based on said detection results by $-(-1)^n$ and applying a low pass filter on this product, and obtaining an imaginary part by dividing said second interference spectrum by the sine of said phase difference; and a process of generating said complex interference spectrum by adding said real part and a product obtained by multiplying said imaginary part by an imaginary unit. Here, n is the identification number of the axial line indicating the position of the A-line in the transverse scanning.

Said imaging step may be configured to include a process of generating, based on the detection results of the interference lights, an interference spectrum that has, as domain of definition, the region having the two phase differences at both ends and that consists of a low frequency part with a background component as its center and a high frequency part present around each of said both ends. Said scanning in said scanning step may be configured to perform at an oversampling ratio at which said low frequency part and said high frequency part are separated.

Said two phase differences may be substantially $+\pi/4$ and $-\pi/4$.

The optical imaging apparatus according to the present invention comprises: a light source; an optical member that divides the light output from said light source into a signal light and a reference light; a scanner that changes the irradiation position of said signal light on an object; a phase changing part that alternately changes the phase difference between said signal light and said reference light to two preset phase differences; an optical member that generates an interference light by combining the signal light passing through said object and the reference light, a detector that detects said interference light; and an imaging part that forms a tomographic image of said object based on the detection results of a plurality of said interference lights sequentially obtained by said detector according to the change in the irradiation position of said signal light.

The apparatus may further comprise a controller that controls said light source and said phase changing part to synchronize the irradiation timing of said signal light on said object and the changing timing of said phase difference.

Said controller may be configured to control said light source to irradiate said signal light on said object at a substantially constant time interval, and to control said phase changing part to alternately change said phase difference at a frequency of substantially ½ of said time interval.

Said phase changing part may be configured to alternately change said phase difference by alternately changing the phase of said reference light between the two preset phases.

Said phase changing part may be configured to alternately change said phase difference by alternately changing the phase of said signal light between the two preset phases.

Said imaging part may be configured to comprise a generator that generates a complex interference spectrum consisting of complex numbers based on the detection results of said interference light, and that forms said tomographic image based on this complex interference spectrum.

Said generator may be configured to: obtain a first interference spectrum by applying a low pass filter to the interference spectrum based on the detection results of said interference light, and obtain a real part by dividing said first interference spectrum by the cosine of said phase difference; obtain a second interference spectrum by multiplying the interference spectrum based on said detection results by $-(-1)^n$ and applying a low pass filter on this product, and obtain an imaginary part by dividing said second interference spectrum by the sine of said phase difference; and generate said complex interference spectrum by adding said real part and a product obtained by multiplying said imaginary part by an imaginary unit.

Said imaging part may generate, based on the detection results of the interference lights, an interference spectrum that has, as domain of definition, the region having the two phase differences at both ends and that consists of a low frequency part with a background component as its center and a high frequency part present around each of said both ends. Moreover, the optical imaging apparatus may comprise a controller that controls said light source and said scanner to scan said object with said signal light at an oversampling ratio at which said low frequency part and said high frequency part are separated.

Said two phase differences may be substantially $+\pi/4$ and $-\pi/4$.

Effects of the Invention

According to the present invention, by forming a tomographic image based on the plurality of detection results sequentially obtained by performing scanning while alternately changing the phase difference between the signal light and the reference light to two phase differences, it is possible to extend the imaging depth range at a lower cost.

BRIEF DESCRIPTION OF THE DRAWINGS

FIG. 9 is a timing chart showing an example of synchronous control performed by the optical imaging apparatus according to the embodiment.

DESCRIPTION OF EMBODIMENTS

Examples of the optical imaging method and the apparatus for performing this method according to the present invention will be described with reference to the figures.

<Description of the Principle>

First, the principle of the optical imaging method according to the embodiment will be described.

In this embodiment, data is acquired by performing transverse scanning (B-scanning) while changing the phase between two values in an alternating manner (i.e., alternately), and a spectral interferogram (complex interferogram or complex interference spectrum) consisting of complex numbers is generated based on the acquired data. Then, by reconstructing the image based on this complex interferogram, a tomographic image (B-scanning image) without a mirror image is obtained. As a result, extension of the imaging depth range, which is the object, is achieved. Moreover, as described later, the apparatus of this embodiment can achieve this object by only slightly adding a configuration to the conventional FD-OCT, i.e., at a lower cost.

Most FD-OCTs perform measurements by combining two scanning modes: A-line scanning and transverse scanning. A-line scanning is a mode for collecting the spectral interferogram in which the profile in the axial line direction of the object is encoded. Specifically, A-line scanning in SS-OCT is a mode for sequentially irradiating light with a plurality of wavelengths on each A-line, and A-line scanning in SD-OCT is a mode for irradiating a broadband light of various wavelengths on each A-line. In addition, transverse scanning is a mode for sequentially scanning a plurality of A-lines in order to form two-dimensional tomographic images. After removing the background component from the collected data, the spectral interferogram collected by transverse scanning is expressed as follows:

$$I(k, n) = \int_{-\infty}^{+\infty} A(z, n)\cos(kz + \varphi_0(z, n)) dz \quad (3)$$

where n is the identification number of the axial line indicating the position of the A-line in transverse scanning.

Transverse scanning is synchronized with A-line scanning by certain signals such as A-line trigger signals. The A-line trigger signal indicates the timing for starting each A-line scanning, and is generated by the wavelength-swept light source driver in SS-OCT or the interference light detection module in SD-OCT. The transverse scanning rate $f_s$ is defined as the repetition frequency for A-line scanning. Since a plurality of A-lines are generally aligned at a constant interval along the transverse scanning direction, the transverse scanning rate $f_s$ can be regarded as the transverse sampling rate.

Figure 1:
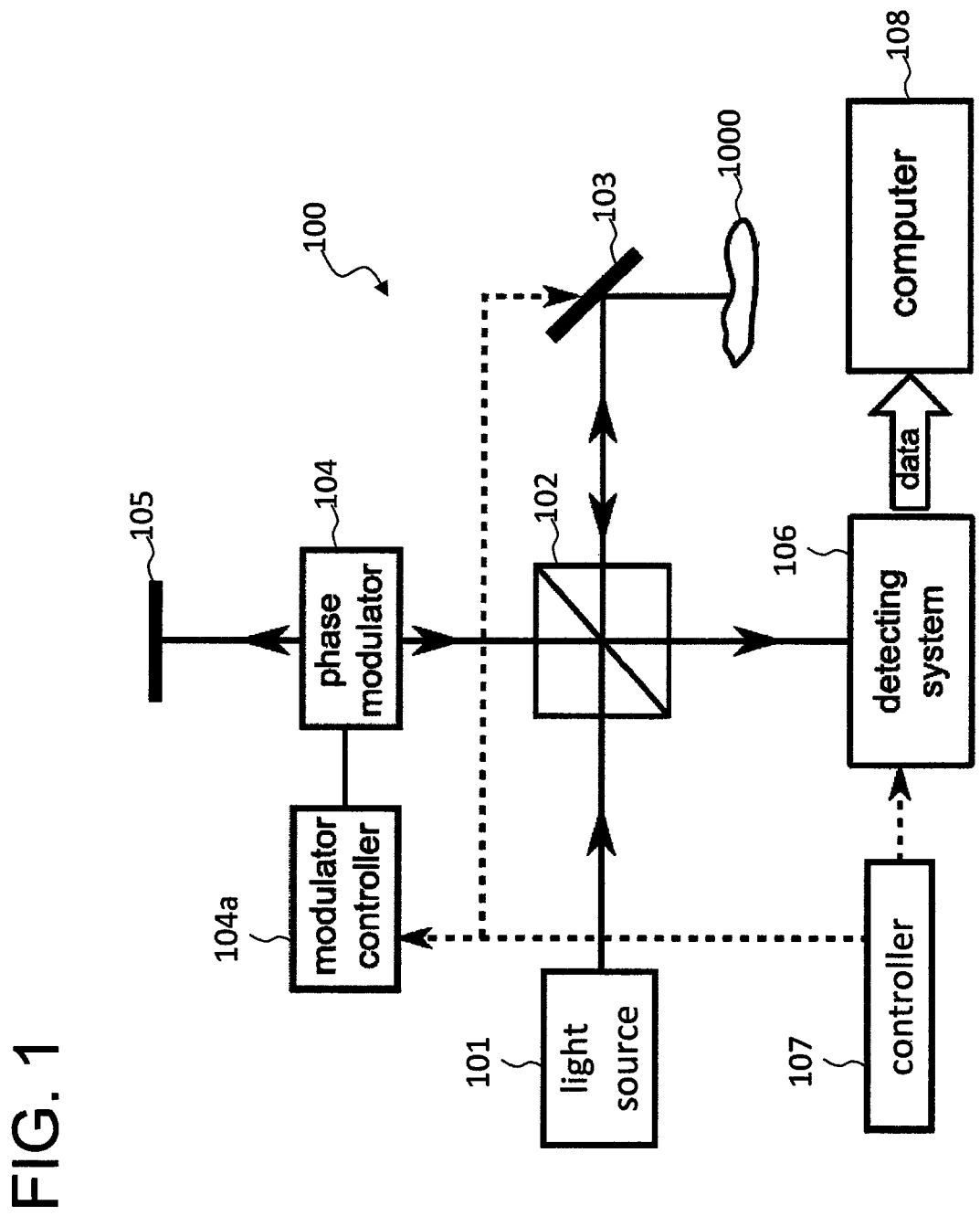
FIG. 1 is a schematic diagram for explaining the principle of an optical imaging method and an optical imaging apparatus according to an embodiment.

A configuration example of the apparatus realizing the principle of this embodiment is shown in FIG. 1. An optical imaging apparatus 100 is an apparatus that forms a tomographic image of an object (sample) 1000, and comprises a light source 101, a beam splitter 102, a scanner 103, a phase modulator 104, a modulation controller 104a, a reference mirror 105, a detection system 106, a controller 107, and a computer 108.

The light output from the light source 101 is divided into a signal light and a reference light by the beam splitter 102. The scanner 103 scans the object 1000 with the signal light. The reflected light and backscattered light of the signal light from the object 1000 are returned to the beam splitter 102 through the scanner 103. The phase modulator 104 is controlled by the modulation controller 104a to modulate the phase of the reference light. The reference light is reflected by the reference mirror 105 and returned to the beam splitter 102 by way of the phase modulator once again. The beam splitter 102 superposes the respectively returned signal light and the reference light to generate interference light. This interference light is detected by the detection system 106. The detection system 106 sends the detected data to the computer 108. The computer 108 forms an image of the object corresponding to the scanning range of the signal light based on this detection data. It should be noted that the controller 107 performs synchronization control of the scanner 103, modulation controller 104a, and detection system 106.

The phase modulator 104 is for modulating the phase of light and is installed in the reference arm or the sample arm. It is noteworthy that the phase change used in the present embodiment should be referred to as "phase alternation" rather than phase modulation. Phase alternation means that two phase statuses $+\Delta\phi$ and $-\Delta\phi$ are alternately applied corresponding to the sequential detection of a plurality of A-lines (i.e., corresponding to transverse scanning). In other words, the initial phases in the sequential detection of a plurality of A-lines will be $\Delta\phi, -\Delta\phi, \Delta\phi, -\Delta\phi, \Delta\phi, \ldots$.

Examples of the control for achieving this include a method in which the phase alternation and scanning on a plurality of A-lines are synchronized and the phase alternation is performed at a frequency $f_s/2$ that is ½ the scanning frequency on the A-line (i.e., the transverse scanning rate $f_s$). When this condition is applied, the spectral interferogram to be detected is expressed as follows:

$$I'(k,n) = \int_{-\infty}^{+\infty} A(z, n)\{\cos(kz + \varphi_0(z, n) + (-1)^n \Delta\varphi)\} dz \quad (4)$$

where $\Delta\phi$ is the phase alternation amplitude and is changed by the modulation controller 104a. Further, Equation (4) can be expanded to:

$$I'(k,n) = \int_{-\infty}^{+\infty} A(z, n) \quad (5)$$
$$\{\cos(\Delta\varphi)\cos(kz + \varphi_0(z, n)) - (-1)^n \sin(\Delta\varphi)\sin(kz + \varphi_0(z, n))\} dz$$

The first term in Equation (5) is the same as in Equation (3) except for a weight factor $\cos(\Delta\phi)$. On the other hand, the second term in Equation (5) alternates at the frequency $f_s/2$ due to the existence of the alternating term $(-1)^n$. As a result, the first term and the second term can be separated in the frequency domain. It should be noted that, since the alternating frequency $f_s/2$ is merely half the transverse scanning rate $f_s$, SD-OCT using CCD, for example, can be used for detection.

Figure 2:
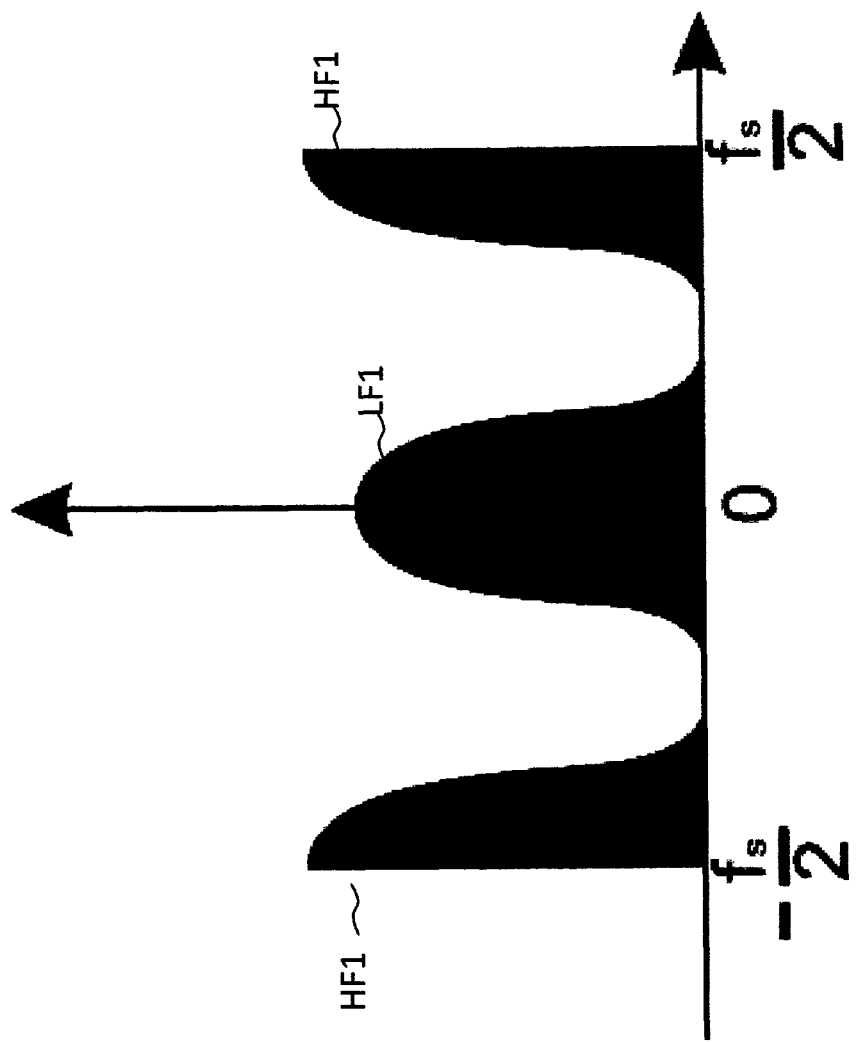
FIG. 2 is a schematic diagram for explaining the principle of the optical imaging method and the optical imaging apparatus according to the embodiment.

FIG. 2 shows an example of the frequency spectrum of I'(k,n) that can be obtained by transverse scanning. This frequency spectrum contains a low frequency part LF1 centered at the background component DC and a high frequency part HF1 centered at the frequency $f_s/2$. The low frequency part LF1 corresponds to the first term in Equation (5) and the high frequency part HF1 corresponds to the second term in Equation (5). According to the Nyquist-Shannon sampling theorem, this spectrum is limited to the range $[-f_s/2, f_s/2]$. Frequencies greater than $f_s/2$ and frequencies less than $-f_s/2$ can be brought to this range by adding $mf_s$. Here, m is a positive or negative integer. For example, $0.6f_s$ becomes $-0.4f_s$ by calculating $0.6f_s+mf_s$ wherein m=-1. Therefore, the high frequency part HF1 shown in FIG. 2 appears on both negative and positive sides in this frequency spectrum.

Because of their frequency difference, the first term and the second term in Equation (5) can be extracted separately as shown in the following equation:

$$\begin{cases} I_{re}(k, n) = \int_{-\infty}^{+\infty} A(z, n)\cos(\Delta\varphi)\cos(kz + \varphi_0(z, n))dz \\ I_{im}(k, n) = \int_{-\infty}^{+\infty} A(z, n)\sin(\Delta\varphi)\cos(kz + \varphi_0(z, n))dz \end{cases} \quad (6)$$

where $I_{im}(k, n)$ can be derived by numerically shifting the frequency of the second term in Equation (2) by $f_s/2$. $I_{re}(k, n)$ and $I_{im}(k, n)$ can be recombined to obtain the complex interferogram as shown in the following equation:

$$I^*(k, n) = \frac{I_{re}(k, n)}{\cos(\Delta\varphi)} + j \cdot \frac{I_{im}(k, n)}{\sin(\Delta\varphi)} \quad (7)$$

$$= \int_{-\infty}^{+\infty} A(\Delta z, n)\cos(2\pi k\Delta z + \varphi_0(\Delta z, n)) + j\sin(2\pi k\Delta z + \varphi_0(\Delta z, n))dz$$

where j is the imaginary unit.

Figure 3:
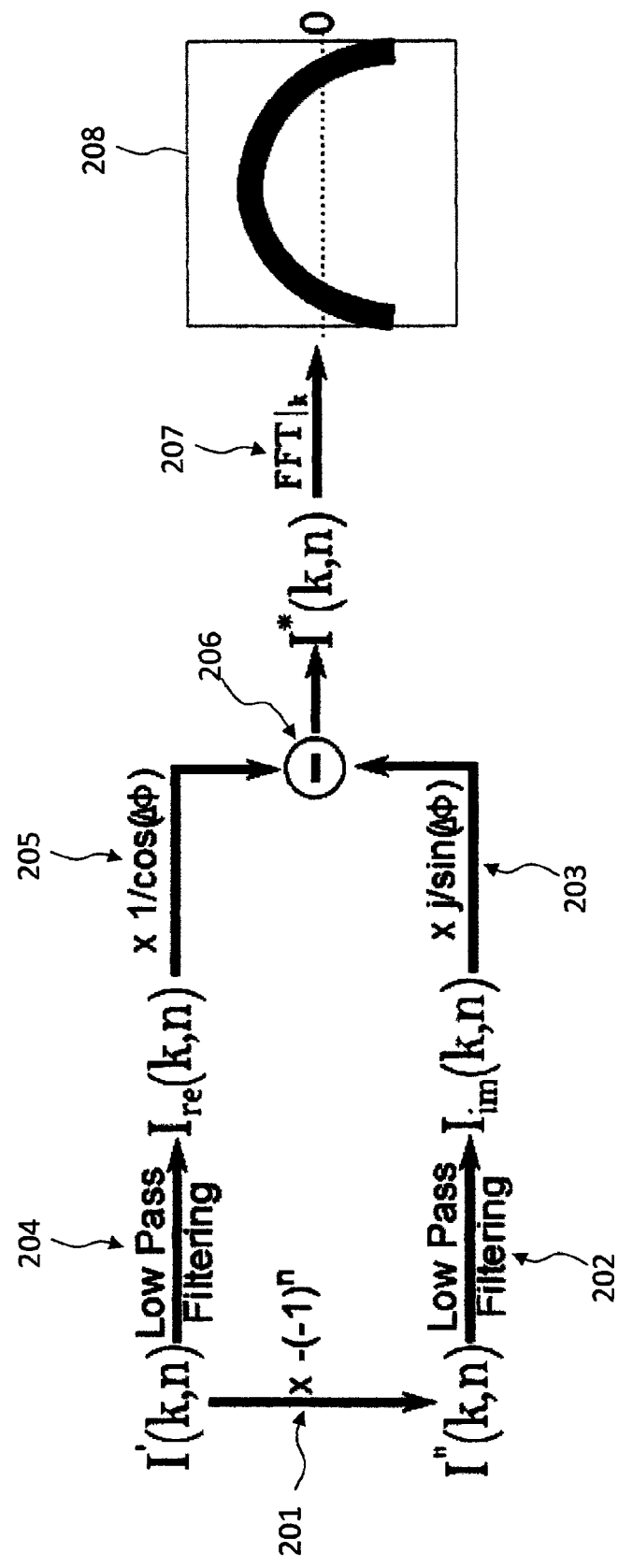
FIG. 3 is a schematic diagram for explaining the principle of the optical imaging method and the optical imaging apparatus according to the embodiment.

FIG. 3 shows an example of the process in which the complex signal $I^*(k, n)$ is generated from the phase alternating signal I'(k, n) and an image is formed. First, as indicated by the symbol 201, a new signal I"(k, n) is generated by multiplying the detected spectral interferogram I'(k, n) by $-(-1)^n$. This operation shifts the second term mentioned above back to the background component, and corrects its sign (±). Next, as indicated by the symbols 204 and 202, a low pass filter in the transverse frequency domain is applied to both I'(k, n) and I"(k, n) to yield $I_{re}(k, n)$ and $I_{im}(k, n)$, respectively, shown in Equation (6). Subsequently, as indicated by the symbols 203, 205 and 206, $I_{re}(k, n)$ and $I_{im}(k, n)$ are combined to generate the complex signal $I^*(k, n)$ shown in Equation (7). Then, as indicated by the symbol 207, fast Fourier transformation is applied to the complex signal $I^*(k, n)$ to reconstruct an image 208 that is free of complex conjugate artifacts.

It should be noted that the operation of multiplying the actually detected signal I'(k, n) by $-(-1)^n$ to generate the signal I"(k, n) corresponds to the demodulation. Consequently, I'(k, n) and I"(k, n) can be regarded as the real part and the imaginary part, respectively, of complex numbers, and the complex interferogram as shown in Equation (7) can be obtained. Then, using this complex interferogram, a FD-OCT image that is free of complex conjugate artifacts can be formed.

Figure 4:
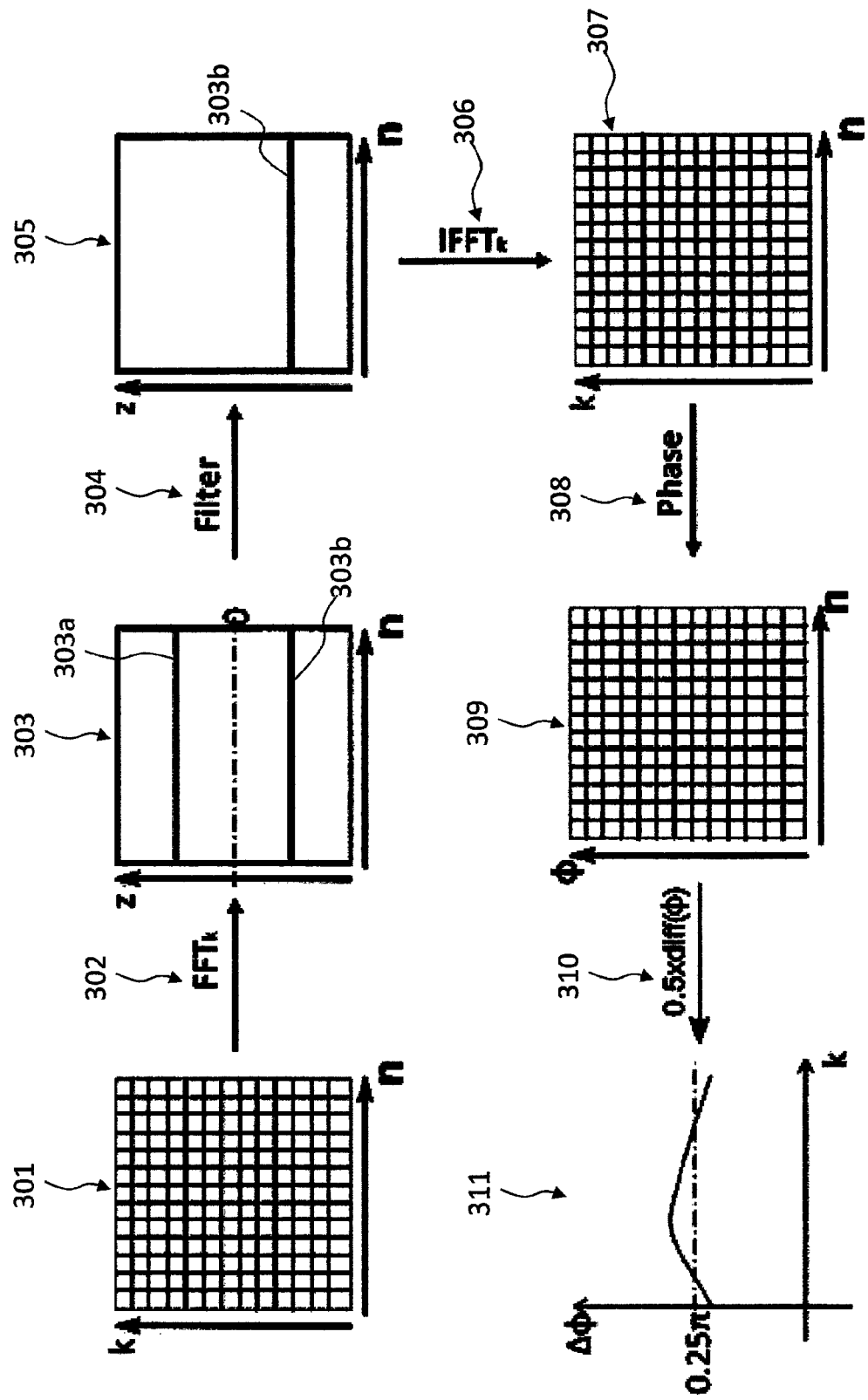
FIG. 4 is a schematic diagram for explaining the principle of the optical imaging method and the optical imaging apparatus according to an embodiment.

In order to obtain the complex signal $I^*(k, n)$ in Equation (7), $\cos(\Delta\varphi)$ and $\sin(\Delta\varphi)$ need to be derived. An example of the process to derive these values will be described with reference to FIG. 4. First, an interferogram 301 corresponding to a single depth is generated by putting a certain object (for example, single surface mirror) into the sample arm and the reference arm, and performing normal FD-OCT measurement. Fast Fourier transformation (302) is applied to this interferogram 301 to form an image 303. A mirror image 303a and a true image 303b of the certain object are drawn in the image 303. Next, the true image b is extracted through the filtering process (304) to form an image 305. Subsequently, inverse fast Fourier transformation (306) is applied to the image 306 to obtain an interferogram 307. Next, the phase of the interferogram 307 for each A-line is calculated as $\phi$. Then, $\Delta\phi$ is obtained as half the value of the phase difference between adjacent A-lines. That is, $\Delta\phi=\{\phi(n)-\phi(n-1)\}/2$, wherein n is an even number. It should be noted that the precision and accuracy of $\Delta\phi$ can be improved by calculating the average using two or more A-lines. By using this $\Delta\phi$, $\cos(\Delta\phi)$ and $\sin(\Delta\phi)$ can be calculated.

Another calculation method of $\Delta\phi$ will be described. The object on which the present embodiment is applied is a scattering medium, which includes biological tissue such as a human retina. In this case, as a more practical approach, $\Delta\phi$ can be statistically estimated by comparing the intensities of $I_{re}(k, n)$ and $I_{im}(k, n)$. For example, the absolute values of $I_{re}(k, n)$ and $I_{im}(k, n)$ are calculated by addition in the transverse scanning direction, and their ratio can be calculated as follows:

$$\frac{\sum_n |I_{im}(k, n)|}{\sum_n |I_{re}(k, n)|} = \frac{\sum_n \int_{-z}^{+z} A(\Delta z, n)|\sin(\Delta\varphi)\sin(k\Delta z + \varphi_0(\Delta z, n))|dz}{\sum_n \int_{-z}^{+z} A(\Delta z, n)|\cos(\Delta\varphi)\cos(k\Delta z + \varphi_0(\Delta z, n))|dz} \quad (8)$$

Considering that in most cases the object in OCT is a turbid scattering medium with randomized $\phi_0(\Delta z, n)$, Equation (8) can be statistically simplified as follows:

$$|\tan(\Delta\varphi)| \approx \frac{\sum_n |I_{im}(k, n)|}{\sum_n |I_{re}(k, n)|} \quad (9)$$

Then, the absolute value of $\Delta\phi$, $|\Delta\phi|$, is then calculated as follows:

$$|\Delta\varphi| \approx a\tan\left(\frac{\sum_n |I_{im}(k, n)|}{\sum_n |I_{re}(k, n)|}\right) \quad (10)$$

Apparently, $\cos(\Delta\phi)$ and $\sin(\Delta\phi)$ can be calculated using $\tan(\Delta\phi)$ or $\Delta\phi$. The sign of $\tan(\Delta\phi)$ or $\Delta\phi$ is either positive or negative, but its sign is not critical since both cases provide images that are free from complex conjugate artifacts. However, when needed, their sign can be obtained as the sign of the phase between odd and even A-lines. For example, assuming that the total number of A-lines constructing one image is N (N is an even number), the image to be reconstructed is expressed as follows:

$$A(z,n) = \text{FFT}|_k(I^{(k,n)}) \quad (11)$$

Then, the signs of $\tan(\Delta\phi)$ and $\Delta\phi$ can then be obtained as follows:

$$\text{sign}(\Delta\varphi) = \text{sign}\sum_{n=1}^{N/2}(\text{angle}(A(z, 2n)) - \text{angle}(A(z, 2n-1))) \quad (12)$$

In most cases, $\Delta\phi$ is a function of the wave number k. Therefore, the statistically estimated $\tan(\Delta\phi)$ or $\Delta\phi$ is a curve along the wave number k that is smoothened, e.g., by curve fitting or filtering to eliminate the statistical noise. In order to achieve the best image quality and maximization of the extent of suppression of the complex conjugate artifacts, the intensities of $I_{re}(k, n)$ and $I_{im}(k, n)$ need to be balanced to avoid large errors occurring in each part. This means $\tan(\Delta\phi) \approx 1$, i.e., $\Delta\phi \approx \pi/4$ would be an optimal number. It is also possible to tune the phase modulator 104 to obtain a $\Delta\phi$ so that $\tan(\Delta\phi) = 1$ for the entire spectrum. Therefore, the complex interferogram shown in Equation (7) is further simplified as follows:

$$I^*(k,n) = I_{re}(k,n) + j \cdot I_{im}(k,n) \quad (13)$$

That is, by determining the frequency of the phase alternation such that $\Delta\phi \approx \pi/4$, this embodiment is particularly effective for scattering mediums such as living tissue, for example, the human retina.

Figure 5A:
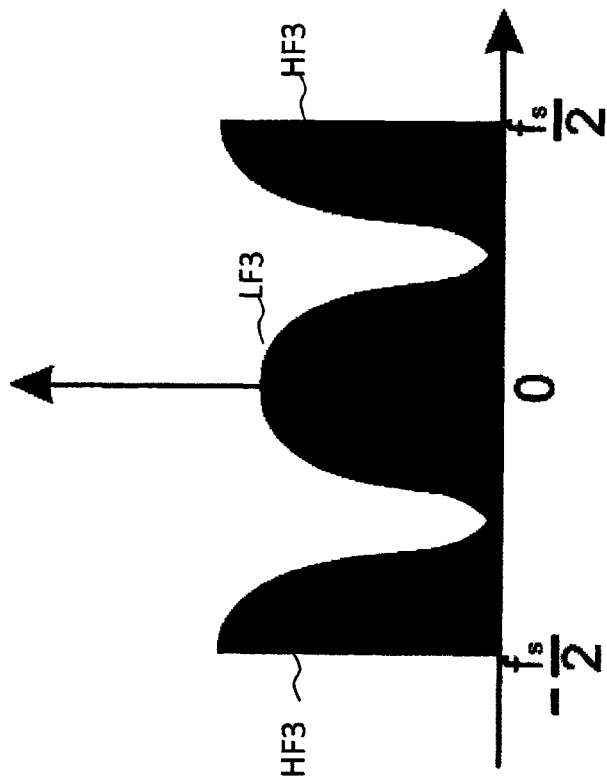
FIG. 5A is a schematic diagram for explaining the principle of the optical imaging method and the optical imaging apparatus according to the embodiment.
Figure 5B:
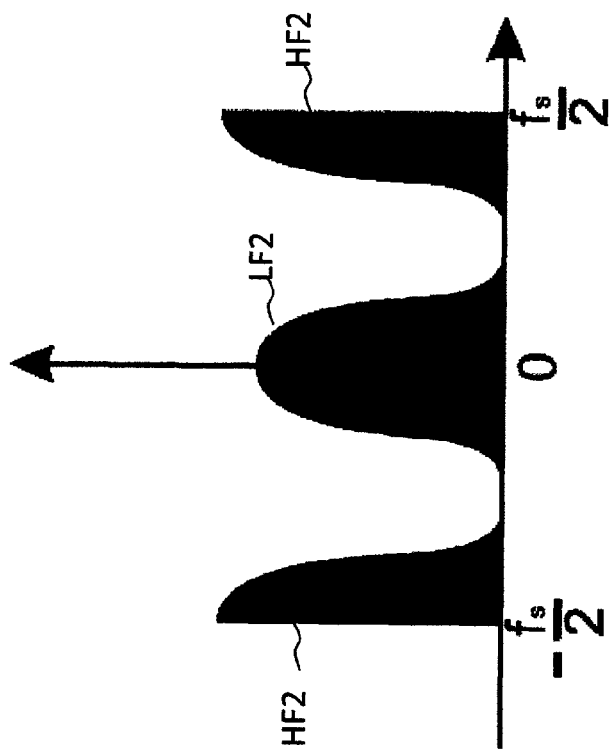
FIG. 5B is a schematic diagram for explaining the principle of the optical imaging method and the optical imaging apparatus according to the embodiment.

In order to unambiguously extract $I_{re}(k, n)$ and $I_{im}(k, n)$ from I'(k, n), it is necessary to optimize transverse oversampling. Oversampling acts to narrow the bandwidth of both the low frequency part and high frequency part, thereby separating the low frequency part LF2 and the high frequency part HF2 as shown in FIG. 5A. In contrast, downsampling broadens the bandwidth of both frequency parts, thereby causing overlapping and aliasing of the low frequency part LF3 and the high frequency part HF3 as shown in FIG. 5B. On the other hand, in order to increase the sampling rate, the number of A-lines needs to be increased, resulting in an undesirable situation in which the load on the apparatus is increased. Therefore, in practice, it is desirable to set an appropriate oversampling ratio to avoid overlapping in the frequency spectrum of I'(k, n) while suppressing the increase in the number of A-lines. In this way, the present embodiment handles only two frequency parts, and optimization of the oversampling ratio is substantially easy as compared to the case in which five or more frequency parts are handled as in patent document 1 and non-patent documents 15, 16 and 18.

Implementation Example

An example of implementing this embodiment will be described below.

[Configuration]

Figure 6:
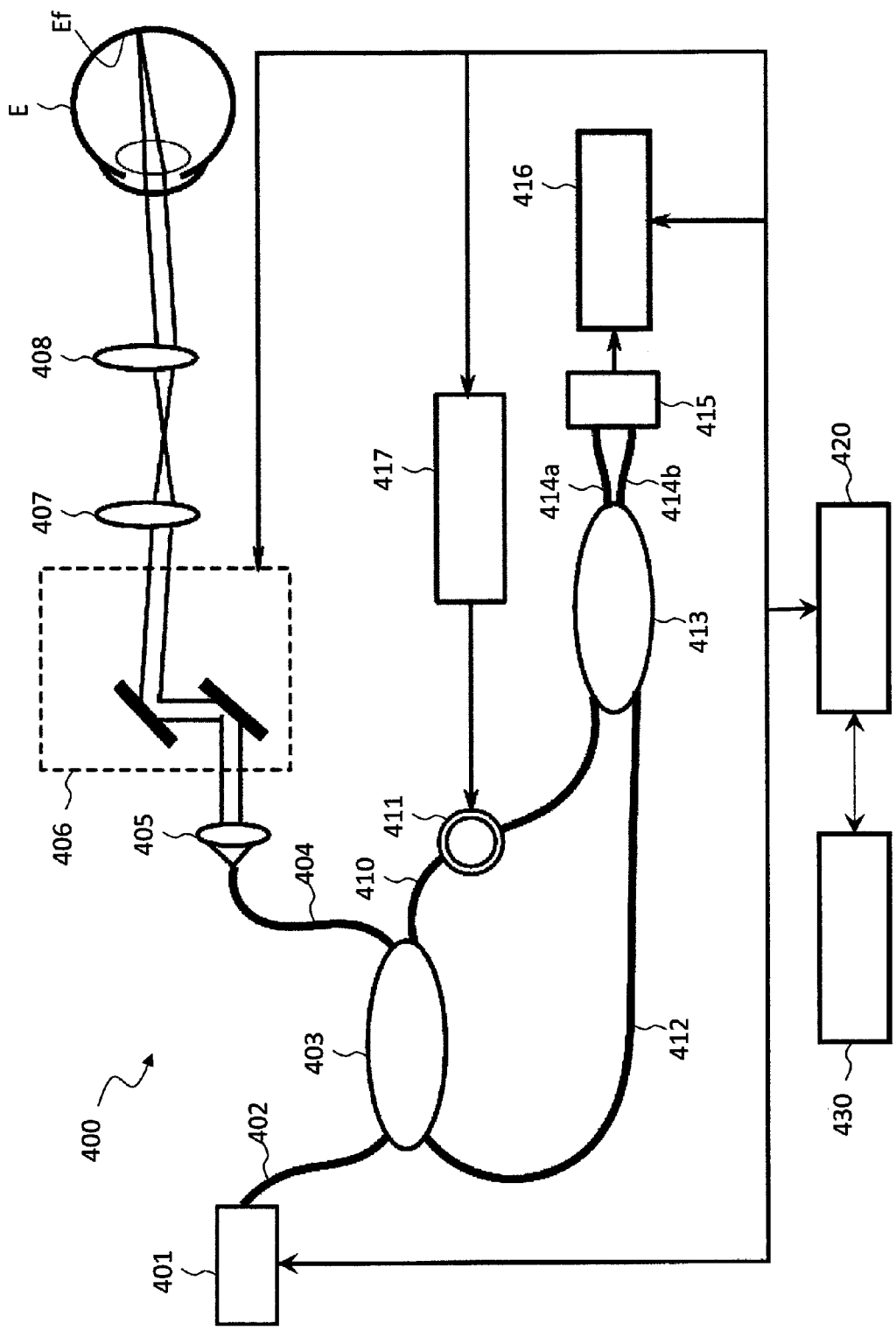
FIG. 6 is a schematic diagram showing an example of a configuration of the optical imaging apparatus according to the embodiment.

A configuration example of the optical imaging apparatus according to this embodiment is shown in FIG. 6. Although an apparatus using SS-OCT will be described herein, a similar configuration can also be applied to an apparatus using SD-OCT. That is, the difference between the apparatus using SS-OCT according the invention and the apparatus using SD-OCT according to the invention is merely the general difference between SS-OCT and SD-OCT.

[Overall Configuration]

An optical imaging apparatus 400 shown in FIG. 6 has a wavelength-swept light source 401 such as a wavelength-variable laser. The wavelength-swept light source 401 outputs a light while continuously changing the wavelength at a high speed. The light output from the wavelength-swept light source 401 travels through an optical fiber 402 and is directed to a fiber coupler 403. The fiber coupler 403 connects four optical fibers 402, 404, 410 and 412 with each other. The light directed by the optical fiber 402 is divided into a signal light and a reference light by the fiber coupler 403. The signal light is a light irradiated on the object, and is also referred to as a measurement light or a sample light. The reference light is combined with the signal light through a predetermined reference path.

The signal light is directed by the optical fiber 404 to be emitted from the fiber end, and made into a parallel pencil by a collimator 405. The signal light that has become a parallel pencil travels through a scanner 406 and is focused on the fundus Ef of an eye E by lenses 407 and 408. The scanner 406 changes the irradiation position of the signal light on the fundus Ef. For the scanner 406, a galvano scanner, a polygon mirror, a resonant scanner, an acousto-optical modulator, a rotating prism, a vibrating prism, etc. are used. The light path created by the optical fiber 404, collimator 405, scanner 406 and lenses 407 and 408 is referred to as, for example, a signal light path or a sample arm.

The signal light irradiated on the fundus Ef is scattered by various tissues of the fundus Ef. Among these scattered lights, backscattered light is returned to the fiber coupler 403 through the signal light path. Moreover, this backscattered light is directed to the fiber coupler 413 by the optical fiber 412. The backscattered light includes depth information of the fundus Ef.

On the other hand, the reference light generated by the fiber coupler 403 is directed to the fiber coupler 413 by the optical fiber 410. A fiber stretcher 411 is provided on the way in the optical fiber 410. The fiber stretcher 411 receives an electrical driving signal from a fiber stretcher driving part 417 and changes the length of the optical fiber 410 by a small amount proportional to the voltage of the driving signal. As a result, the phase of the reference light changes by $\Delta\phi = k\Delta V$. Here, $\Delta V$ is the amplitude of the driving signal. In this way, the fiber stretcher 411 alternatively changes the phase of the reference light between two phases $\pm\Delta\phi$. Consequently, the phase difference between the signal light and the reference light is alternately changed to two preset phase differences. The fiber stretcher 411 constitutes an example of the "phase changing part" along with the fiber stretcher driving part 417. As the phase changing part, not only the fiber stretcher, but also any devices capable of switching two phase statuses can be used, such as an electrical/optical phase modulator, an optical switch, a wave plate, a translation stage, a piezo, etc. The path of the reference light is referred to as a reference light path or a reference arm.

The phase changing part may be provided to only the reference arm as in this embodiment, or may be provided to only the sample arm, or may be provided to both the reference arm and the sample arm. That is, the phase changing part may take any concrete configuration or arrangement as long as it alternately changes the phase difference between the signal light and the reference light to two preset phase differences.

The fiber coupler 413 connects four optical fibers 410, 412, 414a and 414b with each other. The branch ratio of the fiber coupler 413 is, for example, 1:1. The signal light and the reference light are combined by the fiber coupler 413 to generate interference light. This interference light takes over depth information of the fundus Ef included in the signal light and information on the phase change provided to the reference light. A detector 415 detects the interference light directed by the optical fibers 414a and 414b. The detector 415 is a balanced detector that has, for example, two photo detectors and outputs the difference between the detection results by them.

The detector 415 sends its detection results (detected signals) to a data acquisition system 416 every time it detects the interference light. The data acquisition system 416 collects detected signals that are sequentially input from the detector 415. The data acquisition system 416 sends these detected signals to an arithmetic controller 420 collectively, for example, at each series of wavelength sweeps, that is, at for each A-line.

The arithmetic controller 420 reconstructs each A-line profile (A-line image) based on the data input from the data acquisition system 416 using the above-mentioned principle. Moreover, the arithmetic controller 420 forms a B-scanning image (tomographic image) by aligning a plurality of A-line profiles in one column according to the scanning pattern of the signal light. In addition, the arithmetic controller 420 can align a plurality of B-scanning images according to the scanning pattern of the signal light to generate stack data, and can generate volume data by applying image processing such as interpolation to this stack data.

A user interface (man-machine interface) 430 includes a display device, an input device and an operation device. As the display device, for example, an LCD is used. The input device and the operation device include various hardware keys (switch, button, knob, joystick, etc.) provided with the optical imaging apparatus 400. In addition, hardware keys provided with an apparatus (for example, keyboard, pointing device, etc., provided with a computer) connected to the optical imaging apparatus 400 can be used as the input device or the operation device. Moreover, it is also possible to use software keys displayed on the above-mentioned display device or the above-mentioned computer as the input device or the operation device.

[Configuration of the Control System]

Figure 7:
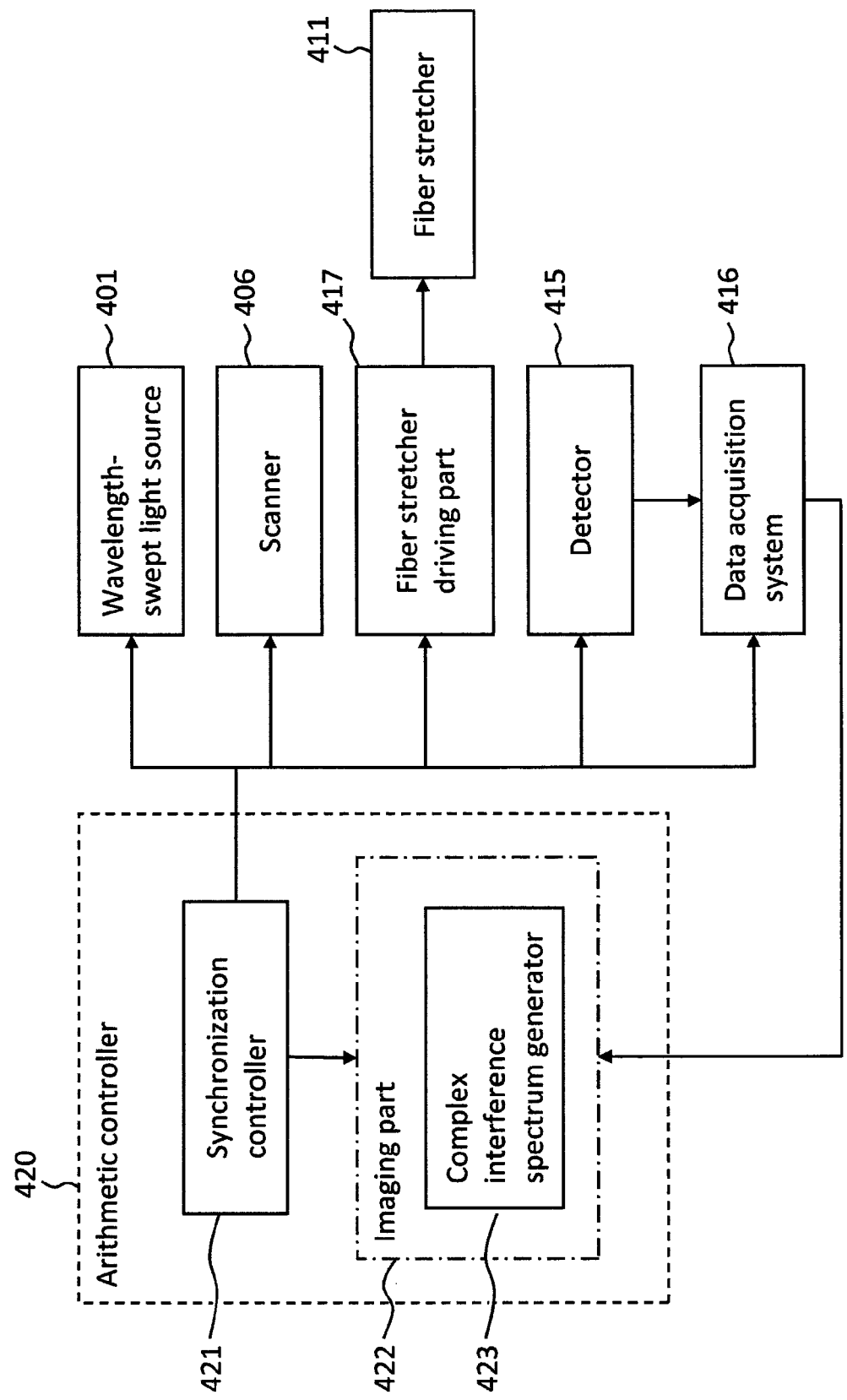
FIG. 7 is a schematic diagram showing an example of a configuration of the optical imaging apparatus according to the embodiment.

A configuration example of a control system of the optical imaging apparatus 400 is shown in FIG. 7.

An arithmetic controller 240 has a function of controlling each part of the optical imaging apparatus 400 and a function of performing various arithmetic processing. The arithmetic controller 420 has a synchronization controller 421 and an imaging part 422. The image controller 422 has a complex interference spectrum generator 423. The synchronization controller 421 is an example of the "controller" and the complex interference spectrum controller 423 is an example of the "generator."

The synchronization controller 421 performs synchronization control for performing OCT measurement. To this end, the synchronization controller 421 controls the wavelength-swept light source 401, the scanner 406, the fiber stretcher driving part 417, the detector 415, and the data acquisition system 416. As a control of the wavelength-swept light source 401, the synchronization controller 421 controls the on/off of the wavelength-swept light source 401 and change of wavelength at a high speed. As a control of the scanner 406, the synchronization controller 421 changes the irradiation position of the signal light on the fundus Ef by, for example, changing the direction of the galvano mirror. As a control of the fiber stretcher driving part 417, the synchronization controller 421 sends a signal to drive the fiber stretcher 411 to the fiber stretcher driving part 417. As a control of the detector 415, the synchronization controller 421 controls the timing to detect the interference light and the timing to output the detected signal. As a control of the data acquisition system 416, the synchronization part 421 causes to output the acquired data.

Synchronization control performed by the synchronization controller 421 will be described. The synchronization controller 421 sends a control signal to each part that is a control target. This control signal is an electrical signal including a frequency component of the transverse scanning rate $f_s$ as described above. This control signal is an electrical signal with, for example, the frequency $f_s$. For example, a sinusoidal electrical signal is used as this control signal, but its waveform is not limited to this. It should be noted that, in place of controlling all parts with one type of control signal, two or more control signals can also be used. For example, it is possible to send a control signal with the frequency $f_s$ to the wavelength-swept light source 401 and the scanner 406, and send an electrical signal with the frequency $f_s/2$ to the fiber stretcher driving part 417.

Based on the control signal, the wavelength-swept light source 401 repeatedly outputs the light while changing the wavelength at a high speed. Based on the control signal, the scanner 406 deflects the signal light in the order corresponding to the arrangement of a plurality of A-lines according to the preset scanning pattern. Based on the control signal, the fiber stretcher driving part 417 generates the driving signal for alternately changing the phase of the reference light and sends it to the fiber stretcher 411. By the control signals, the operation of the wavelength-swept light source 401, the operation of the scanner 406 and the operation of the fiber stretcher 411 are synchronized. Thus, the scanner 406 performs transverse scanning on the arrangement of a plurality of A-lines, and the wavelength-swept light source 401 performs A-line scanning in which lights of a series of wavelengths are irradiated on each A-line, and the fiber stretcher 411 performs phase alternation at a frequency that is ½ the transverse scanning rate.

Figure 8:
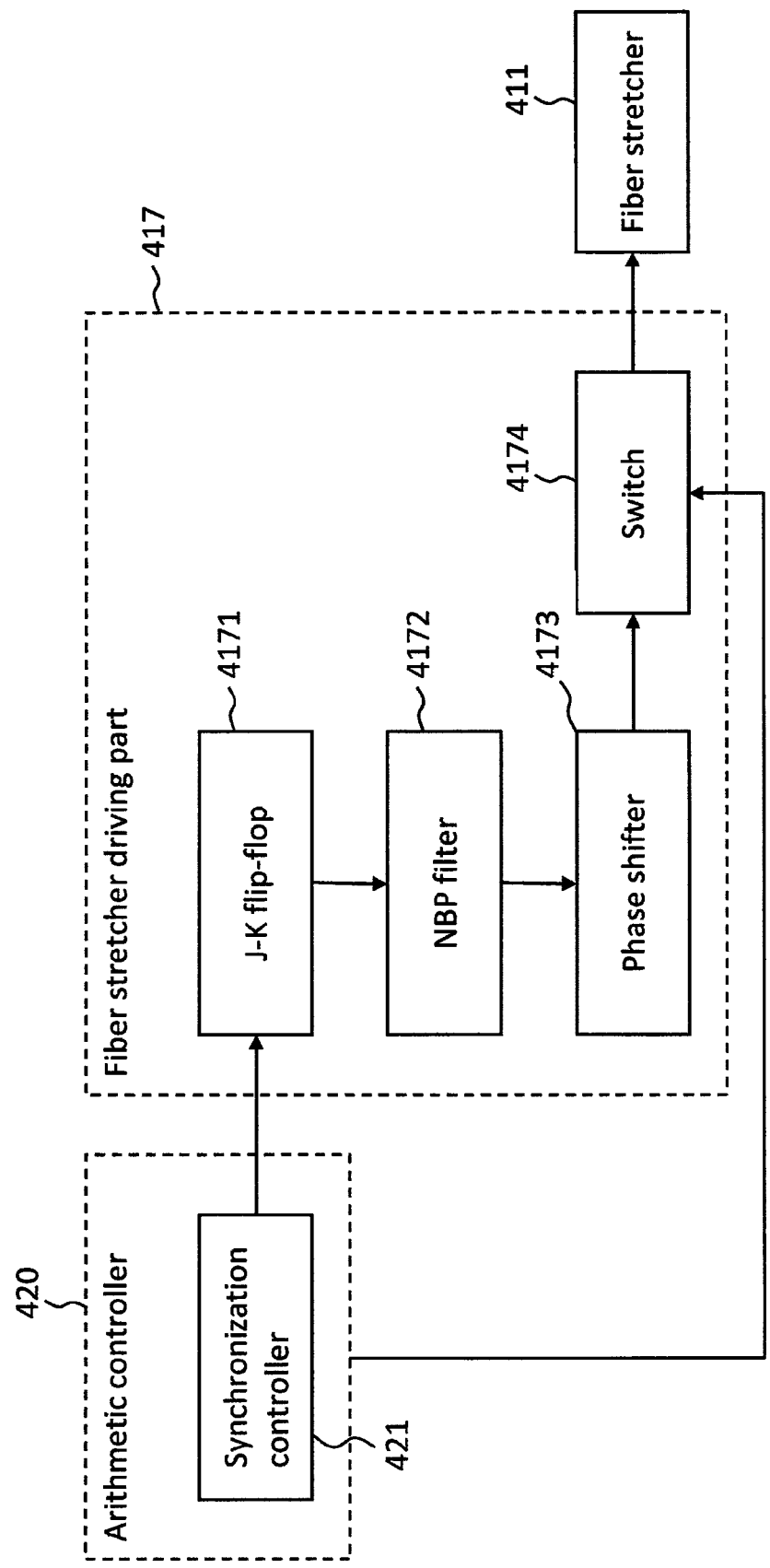
FIG. 8 is a schematic diagram showing an example of a configuration of the optical imaging apparatus according to the embodiment.

The configuration of the fiber stretcher driving part 417 for generating a driving signal with the frequency $f_s/2$ from a control signal with the frequency $f_s$ will be described. This signal conversion processing is performed by, for example, a J-K flip-flop 4171, a narrow band pass (NBP) filter 4172, and a phase shifter 4173 as shown in FIG. 8.

The J-K flip-flop 4171 decreases the frequency $f_s$ of the control signal input from the synchronization controller 421 to half $f_s/2$ and outputs it to a narrow band pass filter 4172. The narrow band pass filter 4172 extracts a first-order harmonic signal, i.e., a sine signal at the frequency $f_s/2$ from the electric signal input from the J-K flip-flop 4171 and outputs it to a phase shifter 4173. The phase shifter 4173, in order to precisely adjust the gap in timing between the A-line acquisition and phase alternation, changes the phase of the sine signal input from the narrow band pass filter 4172 and outputs it to the switch 4174.

The switch 4174 receives (other) control signals from the arithmetic controller 420 and establishes/disconnects the electrical connection between the phase shifter 4173 and the fiber stretcher 411. That is, the switch 4174 establishes the electrical connection when performing measurements according to the present embodiment, and disconnects the electrical connection when performing conventional measurements. The command for such a change in the measurement mode is carried out using, for example, the user interface 430. That is, the user can selectively use the measurement mode according to the present embodiment and the normal, conventional measurement mode.

An example of such a synchronization control is shown in FIG. 9. It should be noted that when controlling the detector 415 and the data acquisition system 416, the same control as that of the wavelength-swept light source 401 or the scanner 406, i.e., the control at the frequency $f_s$, is performed. "A-line identification data (A-line ID)" is the identification data assigned to each of a plurality of A-lines according to the scanning pattern. "A-line trigger" indicates a pulse signal representing the timing of the output of a light for measuring each A-line to the wavelength-swept light source 401. This pulse signal is generated by the driving part (not shown) included in, for example, the wavelength-swept light source 401. It should be noted that the synchronization controller 421 may be configured to generate such pulse signals.

"Driving signal" represents a sine signal that is sent from the fiber stretcher driving part 417 to the fiber stretcher 411. The frequency of the driving signal is half the frequency of the A-line trigger. "Phase alternation status" represents the status of the alternating phase between $+\Delta\phi$ and $-\Delta\phi$, which is specified by the sinusoidal driving signal according to the timing of the A-line trigger. "Phase alternation" represents the status of the phase alternation of the reference light according to the alternating phase specified from the sinusoidal driving signal.

By performing such synchronization control, the detector 415 sequentially detects the interference light corresponding to the light that is repeatedly output by the wavelength-swept light source 401, and sequentially outputs the resultant electrical signals (detected signals). The data acquisition system 416 collects detected signals that are sequentially output from the detector 415 and sends them to the imaging part 422. In addition, information corresponding to the control signal (for example, A-line identification data) is input to the imaging part 422. Based on this information, the complex interference spectrum generator 423 summarizes the data input from the data acquisition system 416 for each A-line, and generates a complex interference spectrum (complex interferogram) for each A-line according to the above-mentioned principle. The imaging part 422 forms the image for each above-mentioned A-line based on the complex interference spectrum for each A-line. Moreover, the imaging part 422 forms a tomographic image of the object by arranging the images for the plurality of A-lines according to the scanning pattern.

EXAMPLES

The inventors performed measurement of a human eye using such a phase alternating SS-OCT. The oversampling ratio was set to $R_s=8$. Here, the oversampling ratio $R_s$ is determined as a ratio of the focus spot size w and the step size (distance between adjacent A-lines) $\Delta x$ of the transverse scanning as follows: $R_s=w/\Delta x$.

Figure 10A:
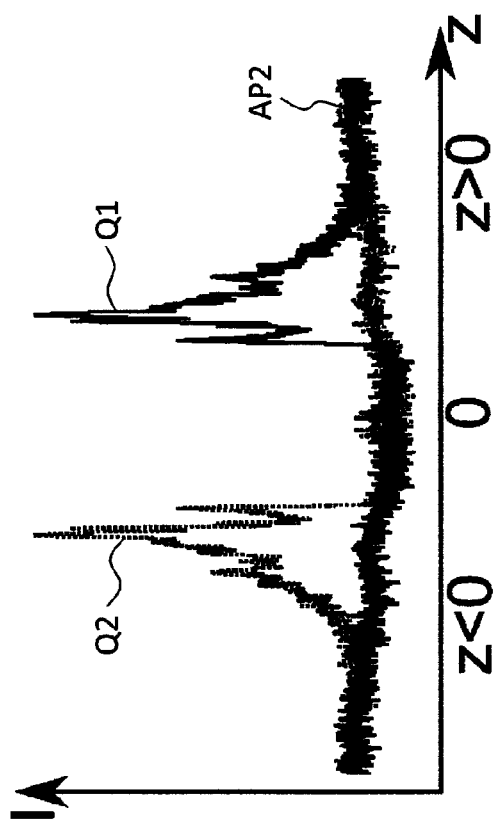
FIG. 10A is a specific example of an A-line profile obtained by the embodiment of the optical imaging apparatus according to the present invention.
Figure 10B:
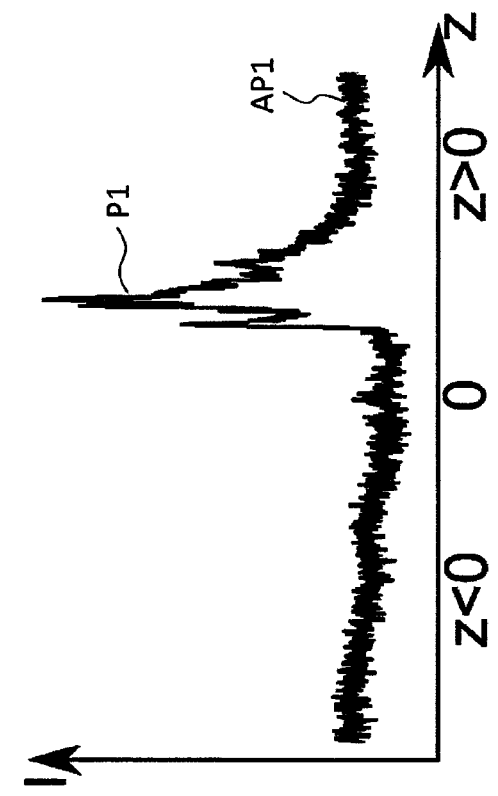
FIG. 10B is a specific example of an A-line profile obtained by a conventional optical imaging apparatus.
Figure 11A:
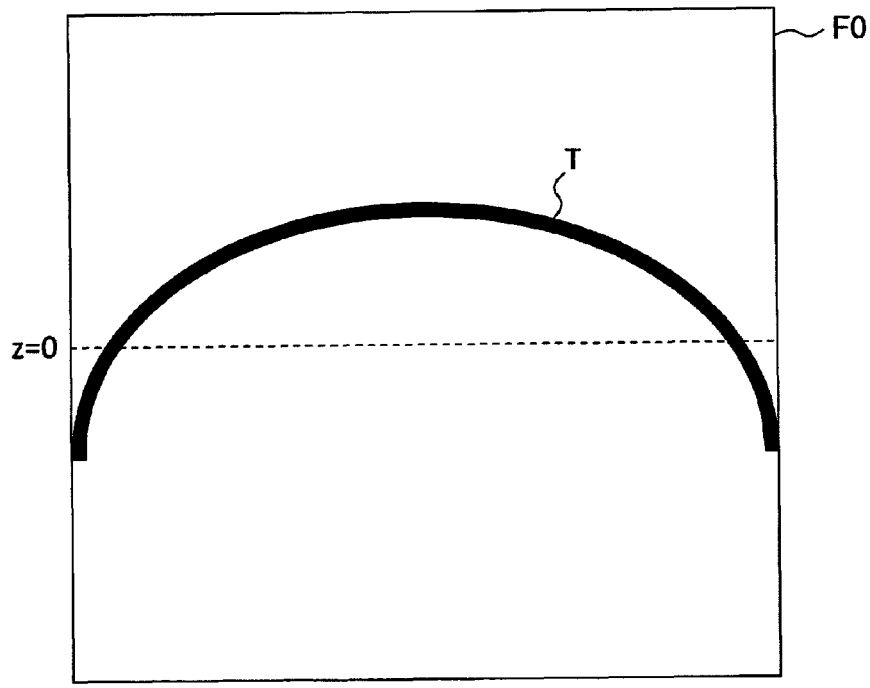
FIG. 11A is a schematic diagram for explaining shrinkage of the possible imaging depth due to the complex conjugate ambiguity.
Figure 11B:
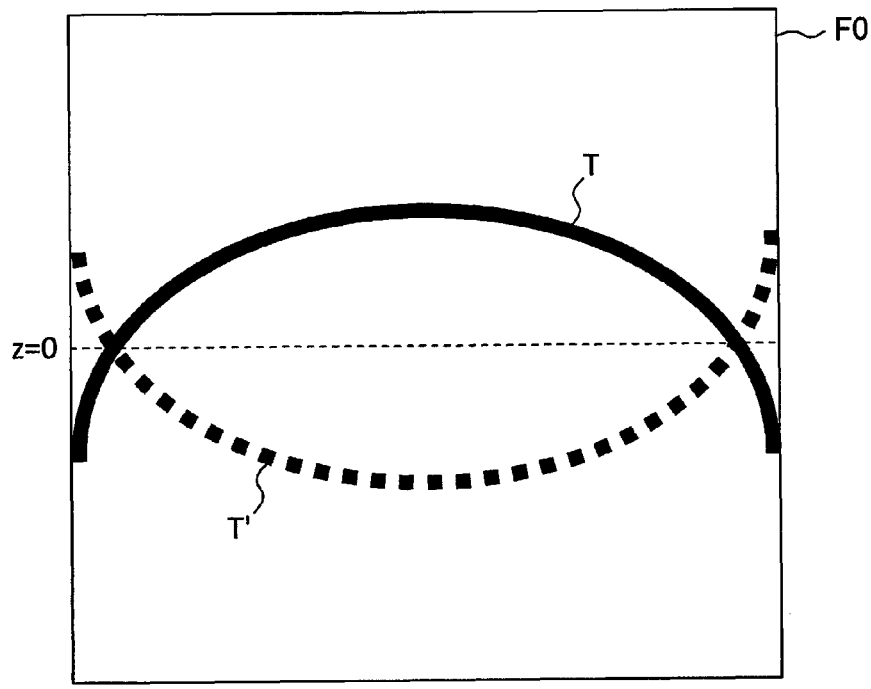
FIG. 11B is a schematic diagram for explaining shrinkage of the possible imaging depth due to the complex conjugate ambiguity.
Figure 11C:
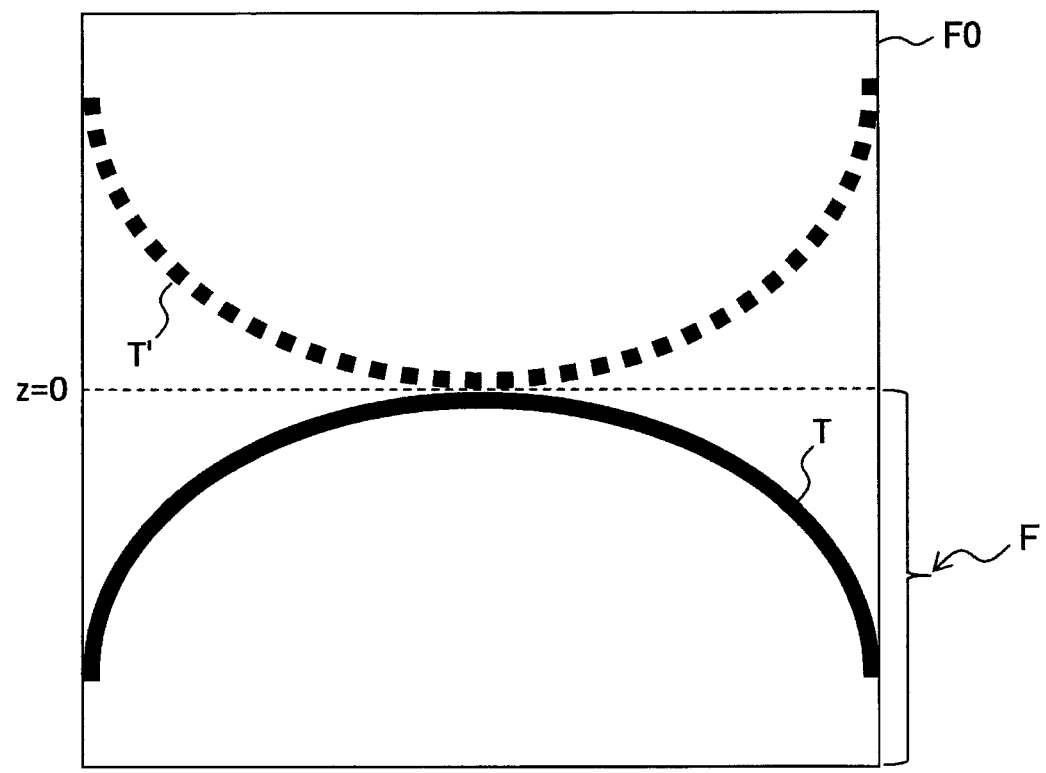
FIG. 11C is a schematic diagram for explaining shrinkage of the possible imaging depth due to the complex conjugate ambiguity.

The A-line profile obtained by this example is shown in FIG. 10A. Moreover, the A-line profile obtained by the conventional method is shown in FIG. 10B. It should be noted that the lateral axis of each A-line profile indicates the depth z, and the longitudinal axis indicates the intensity I of the backscattered light.

The A-line profile AP2 according to the conventional method includes a true image Q1 as well as its complex conjugate, a mirror image Q2. On the other hand, the A-line profile AP1 according to the present example does not have a mirror image, and includes only a true image P1.

[Operation]

The operation of the present embodiment will be described.

The optical imaging apparatus 400 according to the present embodiment forms a tomographic image of an object by processing an interference spectrum based on interference lights that are obtained by combining signal lights passing through the object and reference lights, and performs the scanning step, the detection step, and the imaging step.

In the scanning step, the optical imaging apparatus 400 scans the object with the signal light while alternately changing the phase difference between the signal light and the reference light to two preset phase differences. This scanning step is performed by the wavelength-swept light source 401, the scanner 406, the fiber stretcher 411, the fiber stretcher driving part 417, etc., under the control of the synchronization controller 421.

In the detection step, interference light of the signal light passing through the object and the reference light is detected. This detection step is performed by the detector 415 and the data acquisition system 416 in parallel with the scanning step.

In the imaging step, a tomographic image of the object is formed based on the detection results of a plurality of the interference lights sequentially obtained in the detection step according to the scanning. This imaging step is performed by the imaging part 422.

In the scanning step, scanning can be performed by sequentially changing the irradiation position of the signal light on the object, as well as the irradiation timing of the signal light on the object and the change timing of the phase difference can be synchronized.

In the scanning step, the signal light may be irradiated on the object at a substantially equivalent interval, and the frequency for the alternating change of the phase difference can be substantially ½ the time interval.

In the scanning step, the alternating change of the phase difference may be performed by alternately changing the phase of the reference light between two phases.

In the imaging step, a complex interference spectrum consisting of complex numbers may be generated based on the detection results of the interference light, and the tomographic image can be formed based on the complex interference spectrum.

The process of generating the complex interference spectrum may include the following three processes:

(1) a process of obtaining a first interference spectrum by applying a low pass filter to the interference spectrum based on the detection results of the interference light, and obtaining its real part by dividing the first interference spectrum by the cosine of the phase difference;

(2) a process of obtaining a second interference spectrum by multiplying the interference spectrum based on the detection results by $-(-1)^n$ and applying a low pass filter to this product, and obtaining its imaginary part by dividing the second interference spectrum by the sine of the phase difference; and (3) a process of generating the complex interference spectrum by adding the real part and a product obtained by multiplying the imaginary part by an imaginary unit.

In the imaging step, it may be configured to perform a process of generating, based on the detection results of the interference lights, an interference spectrum that has, as domain of definition, the region having the two phase differences at both ends and that consists of a low frequency part with a background component as its center and a high frequency part present around each of the above-mentioned both ends; and, in the scanning step, scanning may be performed at an oversampling ratio at which the low frequency part and the high frequency part are separated.

The above-mentioned two phase differences may be substantially +π/4 and −π/4.

[Effects]

The effect of the present embodiment will be described.

According to the present embodiment, a complex interference spectrum is generated by newly introducing the approach of "phase alternation" that can be achieved by a simple configuration, and by reconstructing this, an image that is free of mirror images can be obtained. Consequently, it is possible to extend the imaging depth range at a lower cost. This extension of the imaging depth range is twice that in the conventional case in which the interference spectrum of the real value is generated.

In addition, the phase alternation approach has an advantage in that it can be used in both SS-OCT and SD-OCT.

Moreover, the phase alternation approach has an advantage in that the setting and adjustment of the apparatus are easier and the control to change the phase is easier compared to conventional approaches such as phase shifting, BM mode scanning, and phase modulation.

The approach of the present embodiment is to obtain a series of interference spectra, each encoded by the phase alternation (interference spectra corresponding to a plurality of A-lines arranged in the transverse scanning direction). Therefore, the present approach is essentially different from conventional approaches in which Fourier transformation is applied to each of a plurality of interference spectra.

Moreover, the two phase statuses ±Δϕ in the phase alternation approach may be arbitrary, giving it a significantly high degree of freedom compared to conventional approaches. It should be noted that, as described above, the optimal value for Δϕ is π/4. This is because, when Δϕ=π/4, then cos(Δϕ)=sin(Δϕ), so the real part and the imaginary part in FIG. 5) are multiplied by the same amount, thereby balancing the powers of both parts. It should be noted that the value for Δϕ is not limited to π/4 and may be any value as described above.

In addition, the phase alternation approach is also characterized in that a higher harmonic wave is not present. This is due to the fact that only two phase statuses are used, and is significantly different from the conventional phase modulation associated with a higher harmonic wave. While in the conventional phase modulation approach, it is necessary to prevent a number of harmonic signals from being overlapped with each other, such as 0th order, 1st order, 2nd order, 3rd order, . . . in the order from the background component side, in the present embodiment, it is only necessary to consider the low frequency part and high frequency part as shown in FIG. 5A and FIG. 5B, making calibration easy.

Although the embodiments of the present invention have been described above, the above embodiments are shown by way of example only, and are not intended to limit the scope of the invention. These embodiments can be implemented in various forms other than those described above. That is, any change, i.e., any omission, substitution, modification, etc., may be made without departing from the spirit of the present invention. These embodiments and their modifications are included in the scope and summary of the present invention as well as the equivalents thereof.

EXPLANATION OF THE SYMBOLS

100 Optical imaging apparatus
101 Light source
102 Beam splitter
103 Scanner
104 Phase modulator
104a Modulation controller
105 Reference mirror
106 Detection system
107 Controller
400 Optical imaging apparatus
401 Wavelength-swept light source
402 Optical fiber
403 Fiber coupler
404 Optical fiber
405 Collimator
406 Scanner
407 Lens
408 Lens
410 Optical fiber
411 Fiber stretcher
412 Optical fiber
413 Fiber coupler
414a, 414b Optical fibers
415 Detector
416 Data acquisition system
417 Fiber stretcher driving part
4171 J-K flip-flop
4172 Narrow band pass filter
4173 Phase shifter
4174 Switch
420 Arithmetic controller
421 Synchronization controller
422 Imaging part
423 Complex interference spectrum generator
430 User interface
E Eye
Ef Fundus

What is claimed is:

1. An optical imaging method for forming a tomographic image of an object by processing an interference spectrum based on an interference light that is obtained by combining a signal light passing through said object and a reference light, characterized in that the method comprises:
    a scanning step to scan the object with the signal light while alternately changing the phase difference between the signal light and the reference light to two preset phase differences;
    a detection step to detect the interference light of said signal light passing through said object and said reference light; and
    an imaging step to form the tomographic image of said object based on the detection results of a plurality of said interference lights sequentially obtained in said detection step according to said scanning.

2. The optical imaging method according to claim 1, characterized in that, in said scanning step, said scanning is performed by sequentially changing the irradiation position of said signal light on said object, and by synchronizing the irradiation timing of said signal light on said object and the changing timing of said phase difference.

3. The optical imaging method according to claim 2, characterized in that, in said scanning step, said signal light is irradiated on said object at a substantially constant time interval, and the frequency for the alternating change of said phase difference is substantially ½ of said time interval.

4. The optical imaging method according to claim 1, characterized in that, in said scanning step, the alternating change of said phase difference is performed by alternately changing the phase of said reference light between two phases.

5. The optical imaging method according to claim 1, characterized in that, in said scanning step, the alternating change of said phase difference is performed by alternately changing the phase of said signal light between two phases.

6. The optical imaging method according to claim 1, characterized in that, in said imaging step, a complex interference spectrum consisting of complex numbers is generated based on the detection results of said interference light, and said tomographic image is formed based on this complex interference spectrum.

7. The optical imaging method according to claim 6, characterized in that the process of generating said complex interference spectrum comprises:
a process of obtaining a first interference spectrum by applying a low pass filter to the interference spectrum based on the detection results of said interference light, and obtaining a real part by dividing said first interference spectrum by the cosine of said phase difference;
a process of obtaining a second interference spectrum by multiplying the interference spectrum based on said detection results by $-(-1)^n$ and applying a low pass filter on this product, and obtaining an imaginary part by dividing said second interference spectrum by the sine of said phase difference; and
a process of generating said complex interference spectrum by adding said real part and a product obtained by multiplying said imaginary part by an imaginary unit.

8. The optical imaging method according to claim 6, characterized in that:
said imaging step includes a process of generating, based on the detection results of the interference lights, an interference spectrum that has, as domain of definition, the region having the two phase differences at both ends and that consists of a low frequency part with a background component as its center and a high frequency part present around each of said both ends; and
said scanning in said scanning step is performed at an oversampling ratio at which said low frequency part and said high frequency part are separated.

9. The optical imaging method according to any one of claim 1, characterized in that said two phase differences are substantially $+\pi/4$ and $-\pi/4$.

10. An optical imaging apparatus comprising:
a light source;
an optical member that divides the light output from said light source into a signal light and a reference light;
a scanner that changes the irradiation position of said signal light on an object;
a phase changing part that alternately changes the phase difference between said signal light and said reference light to two preset phase differences;
an optical member that generates an interference light by combining the signal light passing through said object and the reference light;
a detector that detects said interference light; and
an imaging part that forms a tomographic image of said object based on the detection results of a plurality of said interference lights sequentially obtained by said detector according to the change in the irradiation position of said signal light.

11. The optical imaging apparatus according to claim 10, characterized in that the apparatus further comprises a controller that controls said light source and said phase changing part to synchronize the irradiation timing of said signal light on said object and the changing timing of said phase difference.

12. The optical imaging apparatus according to claim 11, characterized in that said controller:
controls said light source to irradiate said signal light on said object at a substantially constant time interval; and
controls said phase changing part to alternately change said phase difference at a frequency of substantially ½ of said time interval.

13. The optical imaging apparatus according to claim 10, characterized in that said phase changing part alternately changes said phase difference by alternately changing the phase of said reference light between the two preset phases.

14. The optical imaging apparatus according to claim 10, characterized in that said phase changing part alternately changes said phase difference by alternately changing the phase of said signal light between the two preset phases.

15. The optical imaging apparatus according to claim 10, characterized in that said imaging part:
comprises a generator that generates a complex interference spectrum consisting of complex numbers based on the detection results of said interference light; and
forms said tomographic image based on this complex interference spectrum.

16. The optical imaging apparatus according to claim 15, characterized in that said generator:
obtains a first interference spectrum by applying a low pass filter to the interference spectrum based on the detection results of said interference light, and obtains a real part by dividing said first interference spectrum by the cosine of said phase difference;
obtains a second interference spectrum by multiplying the interference spectrum based on said detection results by $-(-1)^n$ and applying a low pass filter on this product, and obtains an imaginary part by dividing said second interference spectrum by the sine of said phase difference; and
generates said complex interference spectrum by adding said real part and a product obtained by multiplying said imaginary part by an imaginary unit.

17. The optical imaging apparatus according to claim 15, characterized in that:
said imaging part generates, based on the detection results of the interference lights, an interference spectrum that has, as domain of definition, the region having the two phase differences at both ends and that consists of a low frequency part with a background component as its center and a high frequency part present around each of said both ends; and
further comprises a controller that controls said light source and said scanner to scan said object with said signal light at an oversampling ratio at which said low frequency part and said high frequency part are separated.

18. The optical imaging apparatus according to claim 10, characterized in that said two phase differences are substantially $+\pi/4$ and $-\pi/4$.

* * * * *